(12) United States Patent
Cai et al.

(10) Patent No.: US 7,202,036 B2
(45) Date of Patent: Apr. 10, 2007

(54) QUENCHING METHODS FOR BACKGROUND REDUCTION IN LUMINESCENCE-BASED PROBE-TARGET BINDING ASSAYS

(75) Inventors: Hong Cai, Los Alamos, NM (US); Peter M Goodwin, Los Alamos, NM (US); Richard A. Keller, Los Alamos, NM (US); Rhiannon L. Nolan, Santa Fe, NM (US)

(73) Assignee: Los Alamos National Security, LLC, Los Alamos, MN (US)

( * ) Notice: Subject to any disclaimer, the term of this patent is extended or adjusted under 35 U.S.C. 154(b) by 291 days.

(21) Appl. No.: 10/460,451

(22) Filed: Jun. 12, 2003

(65) Prior Publication Data

US 2004/0253593 A1 Dec. 16, 2004

(51) Int. Cl.
*C12Q 1/68* (2006.01)
(52) U.S. Cl. .......................................... 435/6
(58) Field of Classification Search ...................... 435/6
See application file for complete search history.

(56) References Cited

U.S. PATENT DOCUMENTS

| | | | |
|---|---|---|---|
| 5,928,862 A | 7/1999 | Morrison | 435/6 |
| 6,350,580 B1 | 2/2002 | Sorge | 435/6 |
| 6,459,805 B1 | 10/2002 | Reynolds et al. | 382/128 |
| 6,528,254 B1 * | 3/2003 | Sorge | 435/6 |
| 2003/0165859 A1 * | 9/2003 | Nazarenko et al. | 435/6 |

OTHER PUBLICATIONS

Nolan et al., Anal. Chem. 75, 6236-6243 (2003).*
R. A. Cardullo et al., "Detection of Nucleic Acid Hybridization by Nonradiative Fluorescence Resonance Energy Transfer", Proceedings of the National Academy of Sciences of the United States of America, vol. 85, Issue 23, Dec. 1, 1988, 8790-8794.
L. E. Morrison, "Homogeneous Detection of Specific DNA Sequences by Fluorescence Quenching and Energy Transfer", Journal of Fluorescence, vol. 9, No. 3, 1999.
M. J. Fiandaca et al., "Self-Reporting PNA/DNA Primers for PCR Analysis", Genome Research, vol. 11: 609-613, 2001.

* cited by examiner

*Primary Examiner*—Kenneth R. Horlick
(74) *Attorney, Agent, or Firm*—Ray G. Wilson; Kenneth K. Sharples (57) ABSTRACT

Background luminescence is reduced from a solution containing unbound luminescent probes, each having a first molecule that attaches to a target molecule and having an attached luminescent moiety, and luminescent probe/target adducts. Quenching capture reagent molecules are formed that are capable of forming an adduct with the unbound luminescent probes and having an attached quencher material effective to quench luminescence of the luminescent moiety. The quencher material of the capture reagent molecules is added to a solution of the luminescent probe/target adducts and binds in a proximity to the luminescent moiety of the unbound luminescent probes to quench luminescence from the luminescent moiety when the luminescent moiety is exposed to exciting illumination. The quencher capture reagent does not bind to probe molecules that are bound to target molecules and the probe/target adduct emission is not quenched.

16 Claims, 10 Drawing Sheets

QUENCHING METHODS FOR BACKGROUND REDUCTION IN LUMINESCENCE-BASED PROBE-TARGET BINDING ASSAYS

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to luminescent probe/target binding assays, where background emission from unbound probes limits sensitivity of target detection.

BACKGROUND OF THE INVENTION

The sensitivity of binding assays in which luminescent probes are used to detect a specific target of interest can be limited by high backgrounds from unincorporated or unbound probes. In heterogeneous assays, such as gel mobility shifts, backgrounds are reduced by physical separation of unbound probes from target-bound probes. However, this requires extra steps and individualized optimization of separation procedures depending on the targets to be analyzed. In some cases, inefficient (low) recovery of the separated targets can greatly decrease the detection sensitivity, requiring greater initial starting amounts of material. Many homogenous binding assays, which do not require separation of unbound from target-bound probes, rely on changes in fluorescence properties for detection. For example, some nucleic acid (NA) detection assays monitor changes in emission color ratios or intensities (fluorogenic polymerase chain reaction (PCR) assays, molecular beacons). While these types of NA detection approaches have helped to reduce backgrounds, they are limited, in part, by difficulties inherent in labeling and purifying dual labeled probes. Therefore, homogeneous assays would benefit from reagents that selectively reduce the emission of non-target bound probes while leaving target probe adducts luminescent.

Various concepts applying fluorescence quenching and energy transfer to reduce the fluorescence background have been applied to hybridization assays of PCR amplified targets, Morrison, L., "Homogeneous Detection of Specific DNA Sequences by Fluorescence Quenching and Energy Transfer," 9 J. of Fluorescence, No. 3, pp. 187–196 (1999). Examples of these techniques are:

1. An adjacent probe format where a fluorescent labeled probe and a quencher probe are designed to bind to adjacent locations on a DNA target; the resulting proximity of the fluorescent label and the quencher act to reduce the fluorescence intensity from the bound fluorescent labeled probes so that a reduction in fluorescence intensity indicates the presence of the target.

2. A complementary probe pair is designed having complementary sequences, one with a fluorescent label and one with a quencher, where the single-stranded complementary probes compete for hybridization with each other and with single-stranded target DNA; the probes bind together in the absence of the target to quench fluorescence from the fluorescent label, but, in the presence of a target, one of the probes preferentially binds to the target sequence so that quenching is reduced.

3. In a variation of approach 1., above, a labeled primer is incorporated in one amplified DNA strand and subsequently hybridizes to a labeled probe that is complementary to the amplified sequence adjacent to the primer position to place the fluorescent label and quencher in an interaction distance to quench fluorescence when the target DNA is present.

4. In a variation of approach 2., above, the termini at one end of the probes are connected to form a hairpin that places the fluorescent label and quencher in a proximity to quench fluorescence in the absence of the target; upon binding to the target the hairpin opens, separating the quencher and the emitter whereby fluorescence from the emitter is observed.

5. In yet another approach, fluorescent-labeled probes and quencher probes are introduced prior to the start of PCR amplification so that DNA polymerase 5'-to-3' exonuclease activity cleaves a single probe strand containing both fluorescent and quencher labels, thereby separating the quencher and emitter during the amplification process.

6. A multi-step PCR detection method is shown, where, following amplification, labeled primer, labeled dideoxynucleosidetriphosphates, and DNA polymerase are added to the reaction mixture. Labeled dideoxynucleotide becomes incorporated to indicate the presence of a particular target nucleotide at that location, thereby placing a second label within interaction distance with the first label of the primer strand.

In all of these cases, both the fluorescent-labeled probe and the quencher probe are present concurrently with the target NA, which increases the complexity of the design by requiring the same conditions for fluorescent labeling and quenching.

Various advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

The present invention is directed to a method for reducing background luminescence from a solution containing unbound luminescent probes, each having a first molecule that attaches to a target molecule and having an attached luminescent moiety, and luminescent probe/target adducts. Quenching capture reagent molecules are formed that are capable of forming an adduct with the unbound luminescent probes and having an attached quencher material effective to quench luminescence of the luminescent moiety. The quencher material of the capture reagent molecules is added to a solution of the luminescent probe/target adducts and binds in a proximity to the luminescent moiety of the unbound luminescent probes to quench luminescence from the luminescent moiety when the luminescent moiety is exposed to exciting illumination. The quencher capture reagent does not bind to probe molecules that are bound to target molecules and the probe/target adduct emission is not quenched.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION

Figure 1:
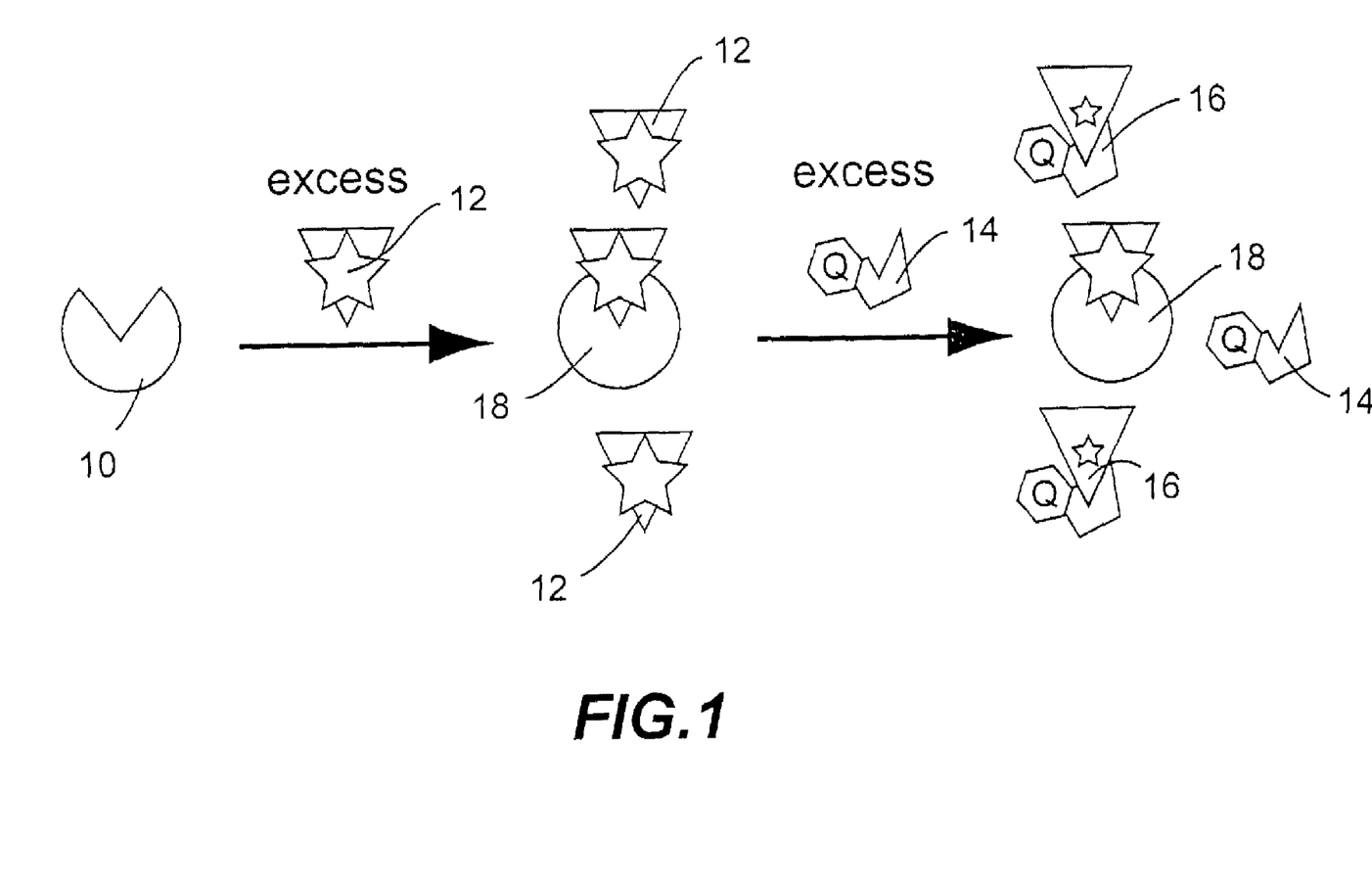
FIG. 1 pictorially illustrates the action of a one-color quencher capture reagent.

In accordance with the present invention as illustrated in FIG. 1, background emission from unbound, luminescent-labeled probes is reduced in luminescence assays. As is well known, a probe molecule is a luminescent molecule that binds specifically to a target 10 that is to be detected. The presence of target 10 is sensitively determined by the detection of luminescence from the luminescent adducts formed by the binding of probes 12 to target 10. However, background emission from unbound probe molecules 12 limits the sensitivity of such assays. In accordance with the present invention, as shown in FIG. 1, luminescence from unbound probes 12 is quenched by the addition of another molecule containing a quencher 14, referred to here as a quenching capture reagent, that binds specifically to the unbound, luminescent-labeled probes 12. Binding 16 of a quenching capture reagent 14 to a luminescent probe 12 brings the quencher moiety of the capture reagent 14 into proximity with the luminescent moiety label of the probe and quenches the probe luminescence by non-radiative energy transfer. Emission from the probe/target adducts 18 is not reduced by the quenching capture reagent 14.

As contemplated herein, luminescence can be quenched by a variety of interactions between the emitter and the quencher including: resonant (Förster) energy transfer, ground-state complex formation, excited-state reactions, and collisional quenching. See "Principles of Fluorescence Spectroscopy," J. R. Lakowicz, 1999, Kluwer Academic/Plenum Publishers, New York and references therein.

Probe-target and probe-quenching capture reagent molecular interactions include: NA-NA, NA-protein, protein-protein, lipid-protein, and the like. Examples of target molecules include: double- and single-stranded nucleic acid oligomers, peptides, proteins, lipids, and carbohydrates. Examples of luminescent probe molecules include: emitting moiety-labeled nucleic acid and nucleic acid analog oligomers, peptides, proteins, lipids, and carbohydrates. Examples of quenching capture reagents include: quencher moiety-labeled nucleic acid and nucleic acid analog oligomers, peptides, proteins, lipids, and carbohydrates.

Luminescent moieties and paired quenching moieties are well known in the art. Luminescent moieties may be fluorescent and selected from the group consisting of organic dyes, proteins, nanostructures, and metals. Likewise, quenching moieties selected from the group consisting of organic dyes, proteins, nanostructures, and metals. Exemplary combinations are illustrated in the following table.

TABLE 1

Exemplary Dye and Quencher Pairs

| Green dye (Em Max) | Green Quencher (Ab Max) | Red dye (Em max) | Red Quencher (Ab max) |
|---|---|---|---|
| Alexa488 (517 nm) | BHQ1 (534 nm) | Alexa647 (668 nm) | BHQ3 (675 nm) |
| FAM (520 nm) | Dabcyl (466 nm) | Cy5 (670 nm) | Cy5Q (644 nm) |
| Rhodamine green (544 nm) | Eclipse (400–650 nm) | | QSY21 (660 nm) |
| | QSY7 (560 nm) | | |
| | QSY9 (562 nm) | | |

As used above, Em Max is the emission wavelength maximum of the dye molecule. Ab max is absorption wavelength maximum of the quencher molecule. Energy transfer between the emission of a fluorophore and absorption of a quencher molecule causes the quenching of the fluorophore.

Figure 2:
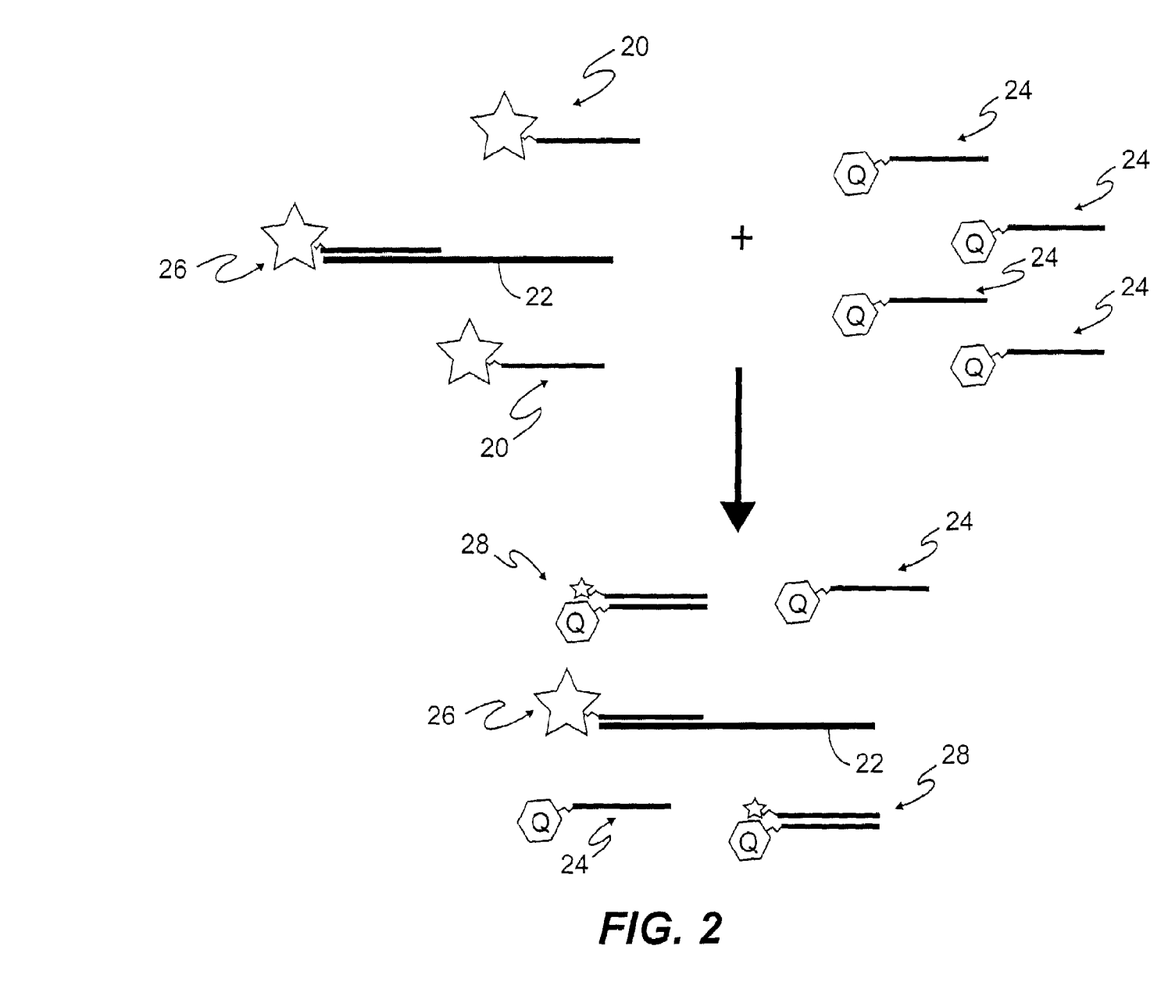
FIG. 2 pictorially illustrates the application of a quencher capture reagent to quench unbound probe luminescence.

FIG. 2 schematically illustrates a first assay of the invention, a one-color bulk fluorescence assay for detection of a single-stranded NA target sequence. Briefly, DNA hybridization probe 20 was used that was complementary to a specific target sequence 22 and was labeled at its 5' end with a fluorophore. A second oligonucleotide 24 complementary to the fluorescently-labeled hybridization probe 20 was labeled at its 3' end with a chromophore designed to efficiently quench the fluorescence of the fluorophore by non-radiative energy transfer. After fluorescent probes 20 are hybridized 26 to the target fragments 22, the quencher-labeled oligonucleotide sequences 24 are added in excess (relative to the probes) to bind 28 and quench unbound fluorescent probes 20 and reduce background fluorescence from unbound fluorescent probes 20.

Figure 3:
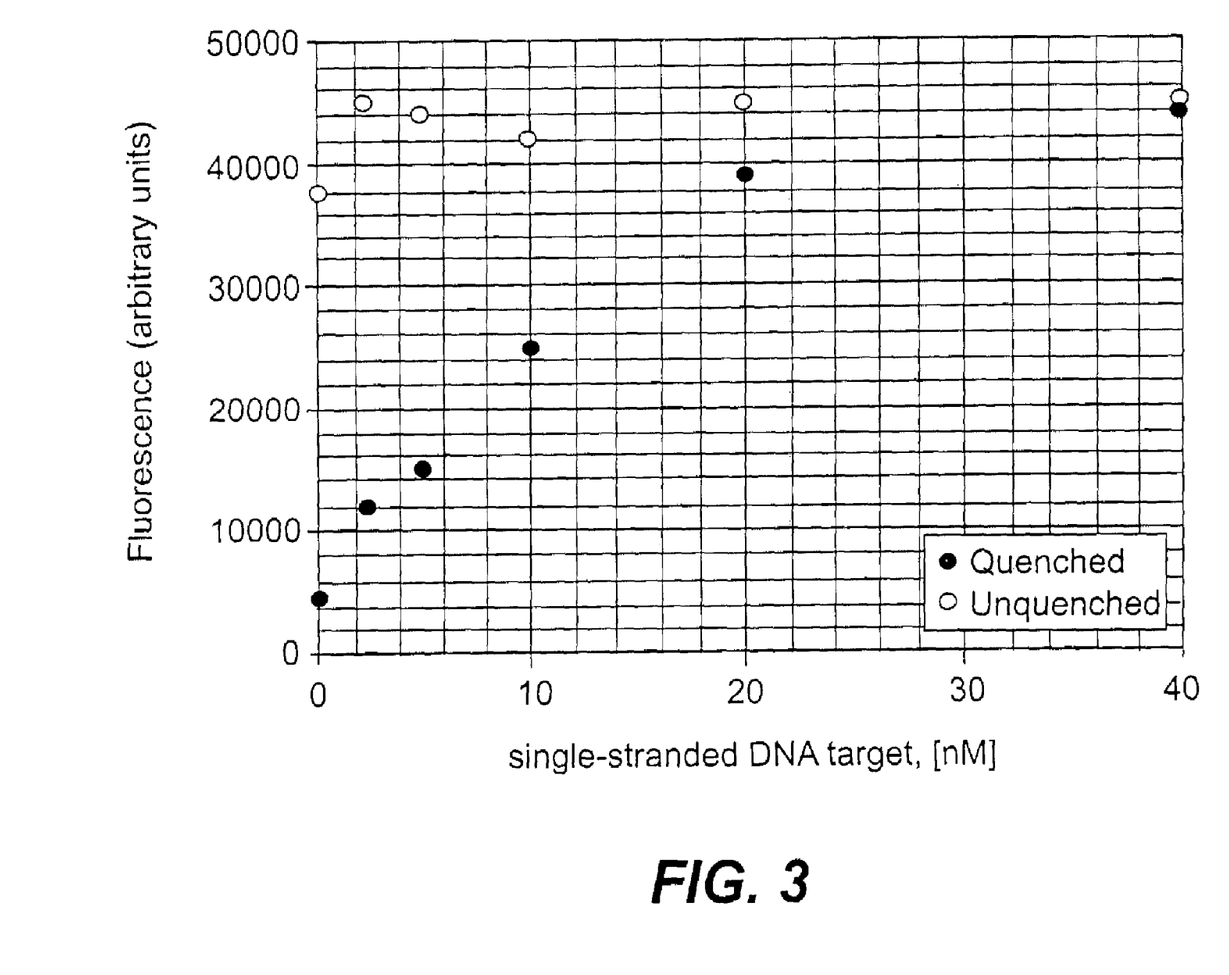
FIG. 3 graphically illustrates the reduction of unbound probe fluorescence in a bulk fluorescence assay for a DNA target as shown in FIG. 2 applied to DNA target oligonucleotides.

FIG. 3 graphically depicts exemplary experimental results that demonstrate effective quenching of unbound probe fluorescence in a bulk measurement using the process depicted in FIG. 2. Using procedures well-known to persons skilled in this art, a bulk assay was run in which a range (0 to 40 nM) of single-stranded DNA target 22 concentrations and 20 nM fluorescent dye-labeled oligonucleotide probes 20 were denatured (95° C. for 5 minutes), annealed (50° C. for 1 hour) and analyzed in a spectrophotometer. Following hybridization of (200 nM) quencher-labeled oligonucleotides 24 to unbound probes 20 (15 minutes at ambient temperature), the samples were re-analyzed to yield quenched data.

Following the probe-target hybridization reaction, the solution fluorescence was measured before and after the addition of varying concentrations of quencher-labeled oligonucleotide 24. Without quencher 24 fluorescence is independent of probe 20 concentration. Upon hybridization of quencher oligonucleotide 24 to unbound probes 20, fluorescence increases with increasing target 22 concentration, saturating at equimolar probe 20 and target 22 concentrations.

Figure 4:
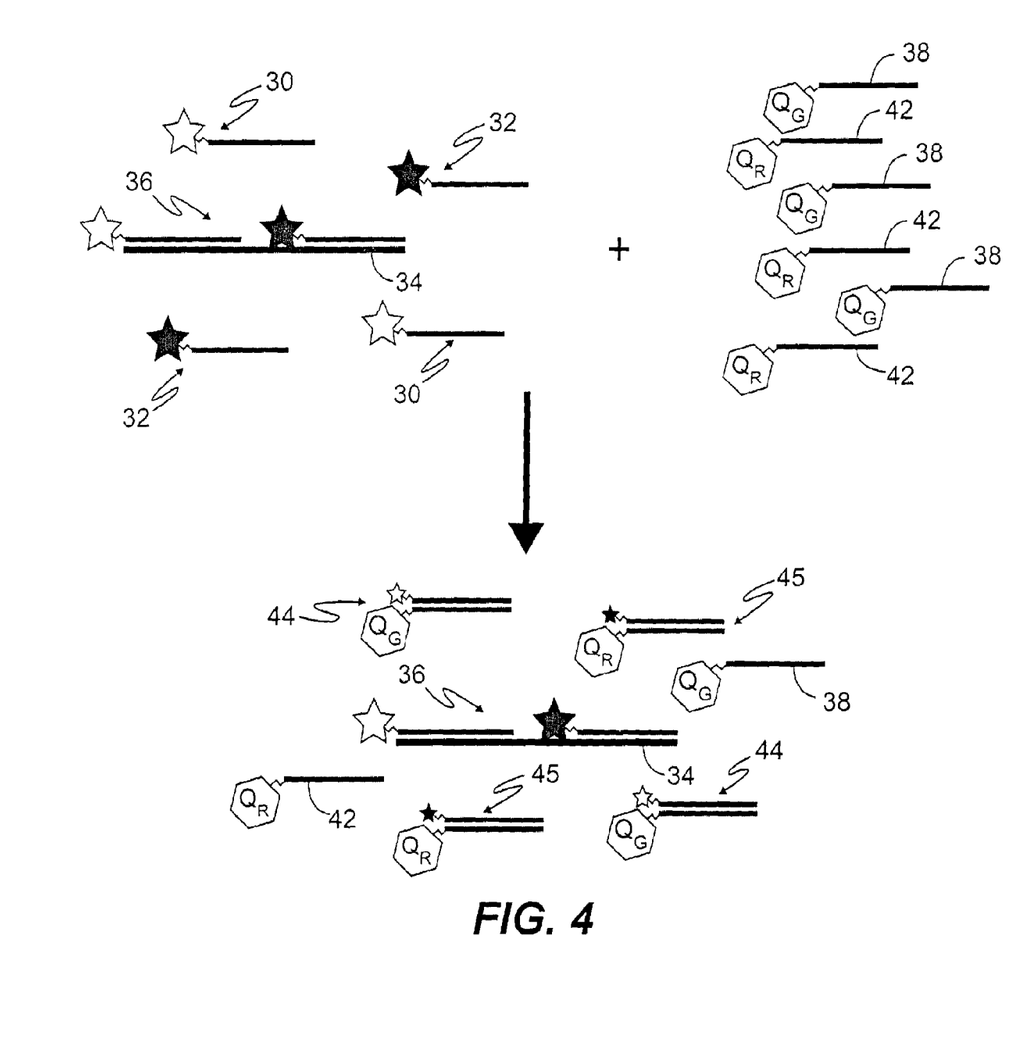
FIG. 4 pictorially illustrates the application of quencher capture reagents to quench unbound probe fluorescence in a two-color assay.

FIG. 4 illustrates application of the present invention to a two-color single-molecule fluorescence detection of a specific nucleic acid sequence, e.g. A. Castro et al, 69 Anal. Chem., Vol. 19, pp 3915–20 (Oct. 1, 1997). Briefly, two hybridization probes 30, 32 that are complementary to specific sub-sequences of a target nucleic acid sequence 34 are labeled at their respective 5' ends with spectrally-distinct fluorophores; in this example, the two are red and green emitting fluorophores. Probes 30, 32 are allowed to hybridize to the target sequence 34. In the case of the target sequence 34, both a green 30 and a red 32 labeled hybridization probe hybridize to the same nucleic acid fragment 34 forming a fluorescent adduct 36 that is co-labeled with a red and a green fluorophore. Background nucleic acid sequences in the sample that do not contain the target sub-sequences do not bind tightly to the hybridization probes. After the hybridization reaction the sample contains primarily the following fluorescent components: (1) unbound fluorescent (green 30 and red 32) hybridization probes, and (2) red-green fluorescent adducts 36 formed from the target sequence and the fluorescent hybridization probes.

In this exemplary two-color assay, the target sequence 34 is detected at the single-molecule level by time-correlated detection of single-molecule fluorescence from the pair of green 30 and red 32 fluorophores co-hybridized to the target fragment 34. These correlated events are detected in the presence of uncorrelated background events due to fluorescence emissions from unbound red- and green-labeled hybridization probes 30, 32 that, by chance, are detected simultaneously. This uncorrelated background scales as the product of the concentrations of the unbound red and green probes. Often, the concentration of the target sequence 34 is low, requiring the addition of fluorescent hybridization probes at high concentrations to increase the speed of hybridization of probes to the target. If this background is too high then the correlated events from the fluorescent probe-target adducts 36 will not be detectable above the background-induced noise.

The method of the present invention provides a lowering of this background and associated noise by reducing the level of fluorescence from unbound hybridization probes, as shown schematically in FIG. 4. Following the hybridization of the fluorescent probes 30, 32 to the target fragments 34, two oligonucleotide probes 38, 42, each complementary to one of the fluorescent hybridization probes 30, 32 are added to the sample. Oligonucleotides 38, 42 are labeled at the 3' ends with moieties designed to quench by energy transfer the fluorophore in the complementary 5'-labeled hybridization probe 30, 32 respectively. Hybridization 44, 45 of a quencher oligonucleotide to an unbound fluorescent probe brings the quencher moiety in close proximity to the fluorophore leading to energy transfer that quenches the fluorophore emission. The quencher oligonucleotides 33, 42 do not bind to the fluorescent probes already hybridized to target sequence fragments and, therefore, these probe-target adducts 36 remain fluorescent.

Unbound probe fluorescence contributes to the baseline of the burst correlation histogram at a rate proportional to the product of the burst detection rates in the detection channels. Shot noise in this baseline determines the detection limit for correlated bursts comprising the peak at zero lag time in the burst cross-correlation histogram. With the use of a quenching strategy as shown in FIG. 4, the background of correlated bursts was decreased approximately 100-fold.

Figure 5:
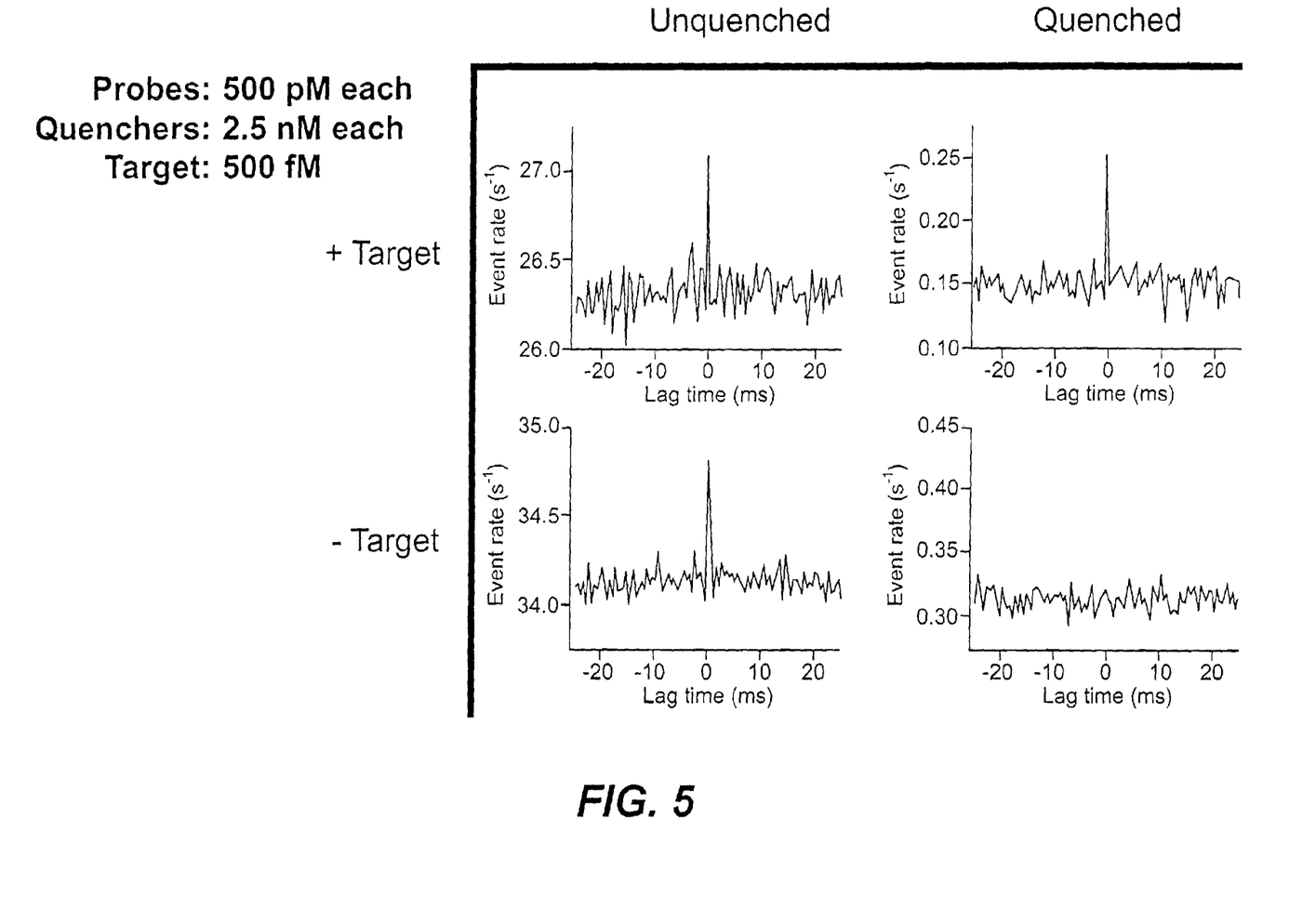
FIG. 5 graphically depicts the increased sensitivity in two-color single-molecule fluorescence-based detection assay using quenching capture reagent.

Two-color single-molecule fluorescence detection of targets using quenching capture reagents is shown in FIG. 5. Single-molecule fluorescence burst correlation histograms were compiled from fluorescence data obtained from samples containing target DNA (a single-stranded 44-mer) at a concentration of 500 fM following hybridization with red and green fluorescent probes at a 1000-fold excess (500 pM probe). All of the samples contained 0.1 mg/ml sheared salmon sperm DNA (average fragment length, ~500 bp) added to reduce loss of probes and targets to container walls. At a target concentration of 500 fM, the concentrations (~500 pM) of the unbound probes were too high to permit reliable detection of the fluorescent probe/target adducts, as shown in FIG. 5. Note that without the quencher capture reagents, correlated bursts were detected both in samples with and without the target. These correlated bursts are attributed to nonspecific binding of the fluorescent hybridization probes to unrelated salmon sperm DNA sequences.

FIG. 5 also shows the improved sensitivity and reduced nonspecific binding obtained after the addition of the quencher capture oligonucleotides to the samples at concentrations of 2.5 nM each. Quenching of the unbound probe fluorescence substantially reduces the background (~100-fold) due to uncorrelated fluorescence bursts, enabling detection of correlated bursts, from the fluorescent probe/target adducts. Additionally, the level of nonspecific binding of the fluorescent probes to unrelated background sequences is reduced with the quencher-labeled capture oligonucleotides. This is due to competition between the quencher-labeled capture oligonucleotides and unrelated (nontarget) sequences as binding sites for the fluorescent probes. The higher binding affinity between the probes and the capture oligonucleotides compared to that between the probes and unrelated background sequences reduces the nonspecific binding.

Figure 6:
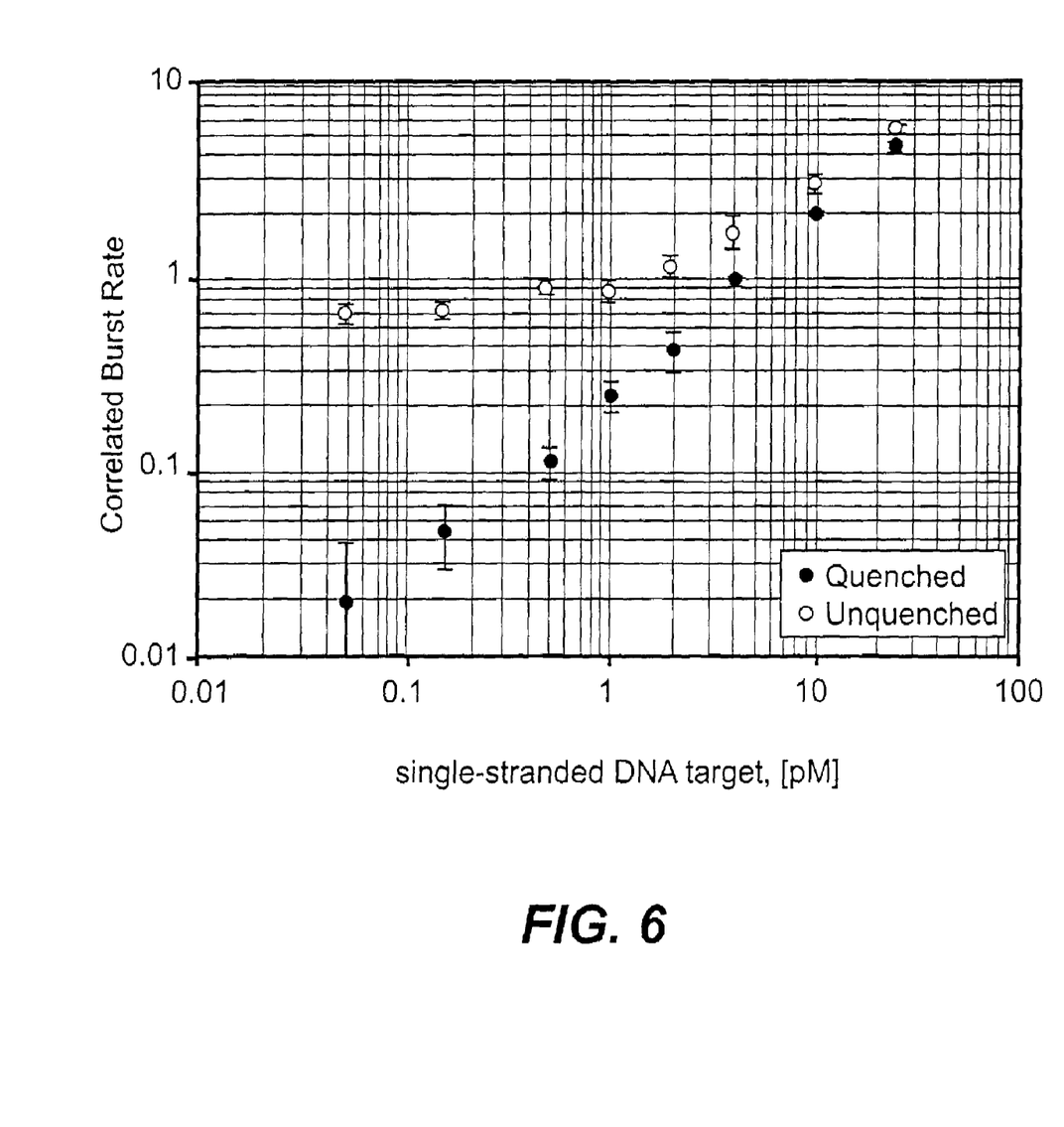
FIG. 6 graphically compares target sensitivities of two-color single-molecule fluorescence with and without quenching of unbound probe fluorescence.

FIG. 6 graphically compares the sensitivity and linearity of two-color single-molecule fluorescence detection of DNA targets with and without the use of quencher-labeled capture oligonucleotides. As shown in FIG. 6, the reduction of unbound probe fluorescence and nonspecific binding obtained with quencher-labeled capture oligonucleotides substantially improve the sensitivity and linearity of the assay.

Figure 7:
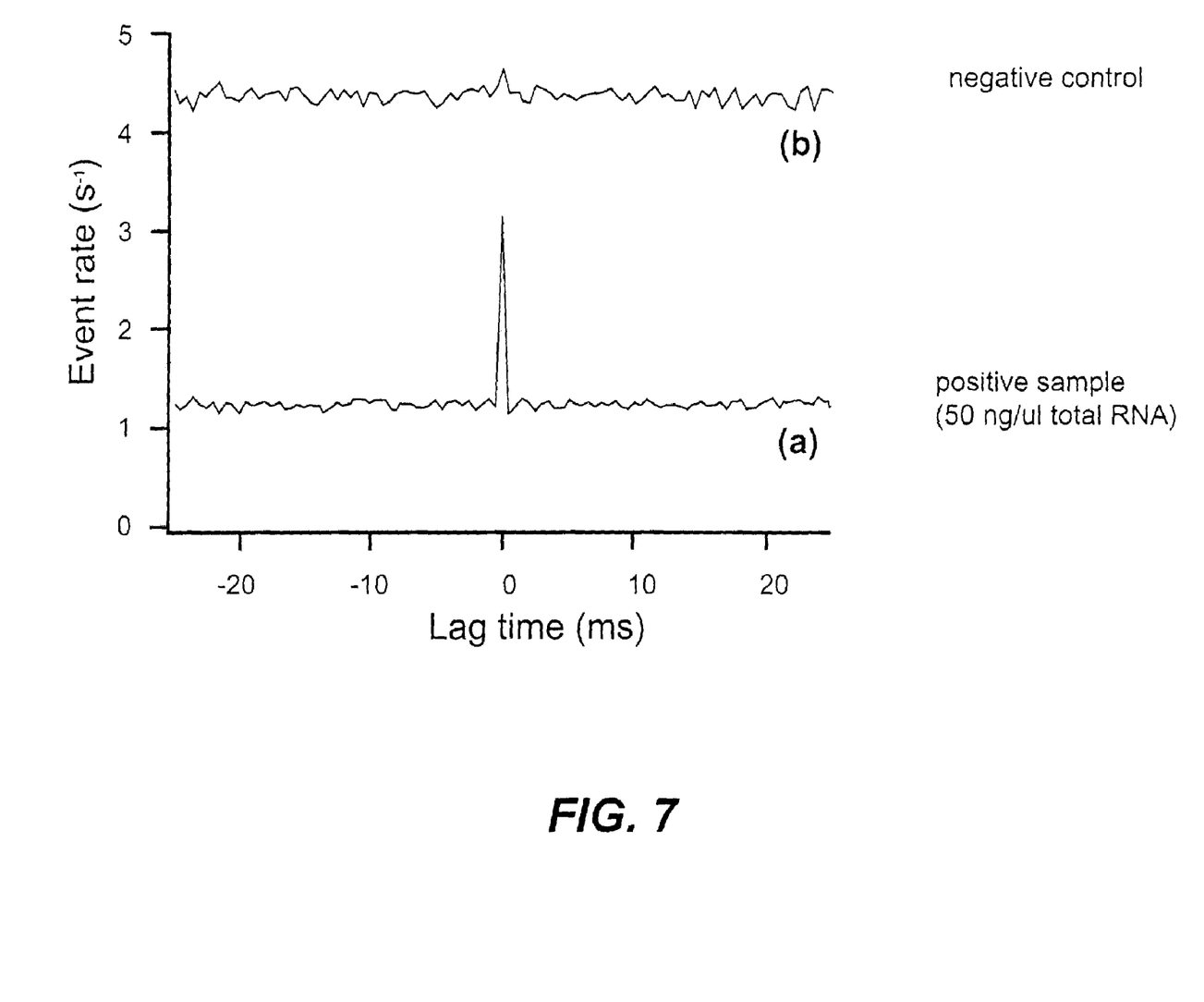
FIG. 7 graphically demonstrates two-color single-molecule fluorescence detection of actin-mRNA in total RNA using quenching capture reagents.

FIG. 7 graphically demonstrates two-color single-molecule fluorescence detection of unamplified actin messenger RNA (mRNA) fragments in total RNA. This was carried out using a pair of fluorescently-labeled oligonucleotide probes each specific to a subsequence of actin mRNA. Use of a pair of quencher-labeled capture oligonucleotides complementary to the probes permits detection of the actin mRNA target in the presence of a ~100-fold excess of the fluorescently-labeled probes.

Figure 8:
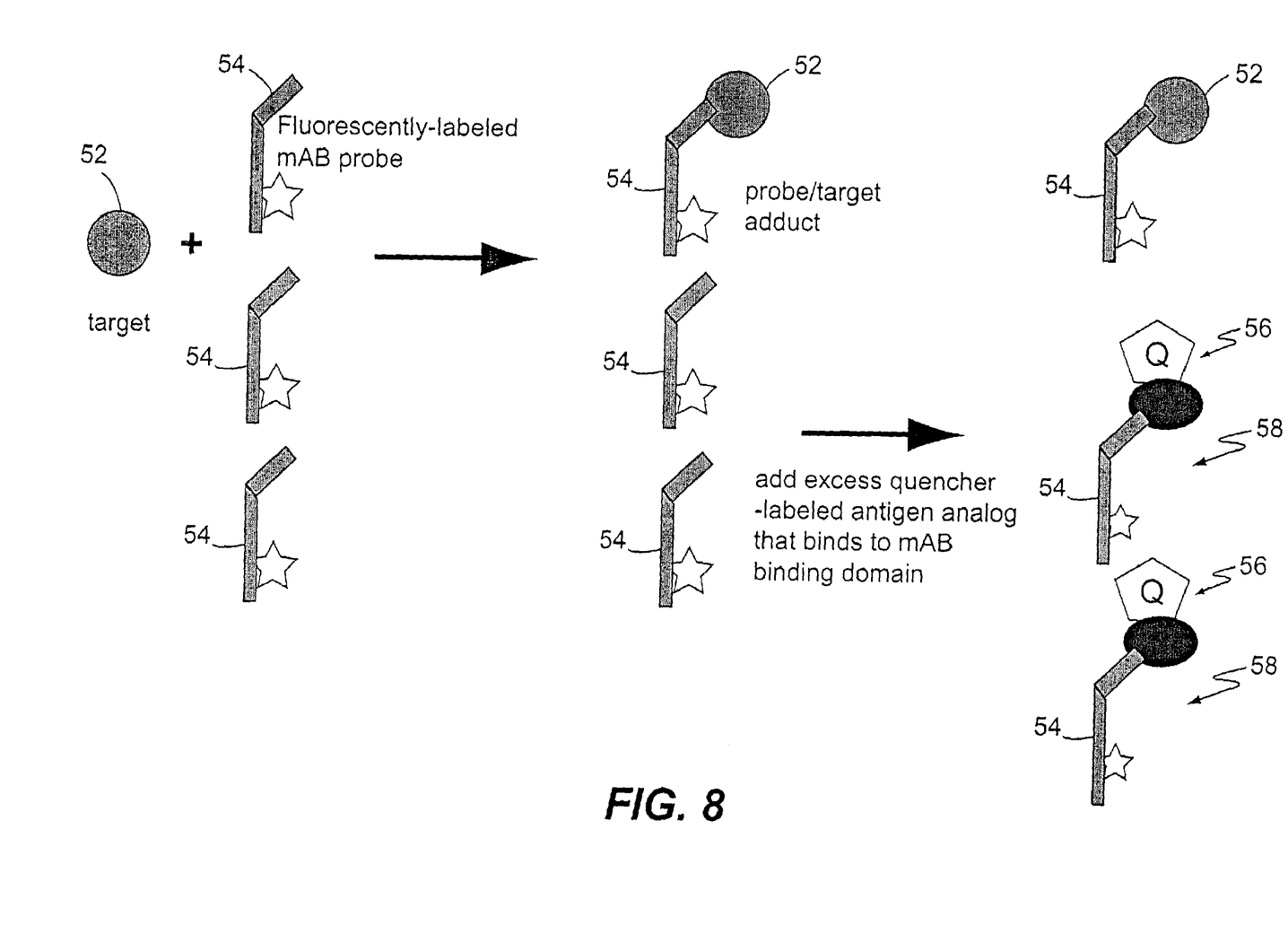
FIG. 8 pictorially demonstrates an example of protein antigen detection by single chain antibody using quenching capture reagents.

FIG. 8 illustrates an example of protein antigen 52 detection by single chain antibody 54 using quenching capture reagents 56. A protein antigen or antigen analog is labeled with a quencher group to form stable quenching molecule-antigen conjugates. The conjugates 56 can be purified on the included size-exclusion spin columns. Suitable labeling protocols are summarized in Hermanson, G. T. et al., *Bioconjugate Techniques*, Academic Press (1996), incorporated herein by reference.

The quencher molecule-labeled antigen 56 is added in large excess to bind 58 to luminescent single chain antibody 54 to quench the emission of unbound single chain antibody.

Other cases of energy transfer among protein-protein molecules are also reported in the literature. Potentially, any protein or ligand that binds to a luminescent antibody can be labeled with quencher molecules and act as capture quenching reagents using protocols that are well known to persons skilled in the art.

It will be appreciated that the detection of the unquenched probe-target molecules can be accomplished using any known luminescence detection system, including single-molecule spectroscopy, flow cytometry, confocal and fluorescence microscopy, gel electrophoresis, fluorimetry (including conventional spectrofluorimeters, plate readers and thermal cycling fluorimeters) and the like.

In another embodiment, the quenching approach can be used in genomic targets using short oligomer probes (30–40 bases at 50–200 pM, Tm ~65 degree) (Han, C. S., et al., *Construction of a BAC contig map of chromosome 16q by two-dimensional overgo hybridization,*" Genome Research, 2000 10(5), pp. 714–721, incorporated herein by reference). Based on these studies, this procedure is capable of labeling ~90% of the unamplified genomic target during an overnight hybridization reaction.

Modifications of the hybridization procedure of Han will be required. Briefly, genomic DNA is blotted onto a membrane denatured at 90° C. for 4 minutes and an allele-specific probe is added for genotyping target hybridization at 58° C. overnight in a buffer containing 0.5 M sodium phosphate, pH 7.2+1 mM EDTA. Unbound probes are then captured and quenched by adding a large excess of quenching capture reagent oligonucleotide at 60° C. for 10 minutes before the measurement. Since the original procedure was developed for capturing a target inside a gel or on a membrane, the hybridization kinetics in solution will be faster. The temperature can be optimized or the salt concentration reduced for quenching capture to reduce the amount of nonspecific hybridization. With the background suppression approach, the background of fluorescence from 500 pM probe will be equivalent to ~10 pM level. Preliminary data, shown in FIG. 6, demonstrates the detection of a 5 pM target using 500 pM probes with the quencher/capture approach. With further optimization, targets at ~100 fM should be detected.

Preliminary data suggest that the capture process can be accomplished in 10 minutes when, e.g., a 5000 pM quencher oligonucleotide concentration is added to capture fluorescent probes at a 500 pM concentration. Since the large excess of quencher capture oligonucleotides (e.g., 5–50 nM) can be used without increased fluorescence background, a 10 minute capture process is expected to be sufficient for background reduction.

In another embodiment, a modified universal two-probe Cleavase genotyping labeling strategy for genotyping may be used. Cleavase assay (also called Invader™ assay developed by Third Wave Technology and Lyamichev, 1999) is a two-primer PCR— and gel-free assay performed on total genomic DNA using universal invader and fluorescent probes and allele-specific signal probes. Cleavase VIII enzyme is a thermostable structure-specific archaebacterial flap endonuclease that cleaves structure-specific rather than sequence-specific sites. This endonuclease has been engineered to recognize and cleave flap sequences at a specific junction of flap/invader/target sequence employed in the Invader™ assay. Genotyping using Cleavase approach was found to be 99.8% accurate.

Figure 9:
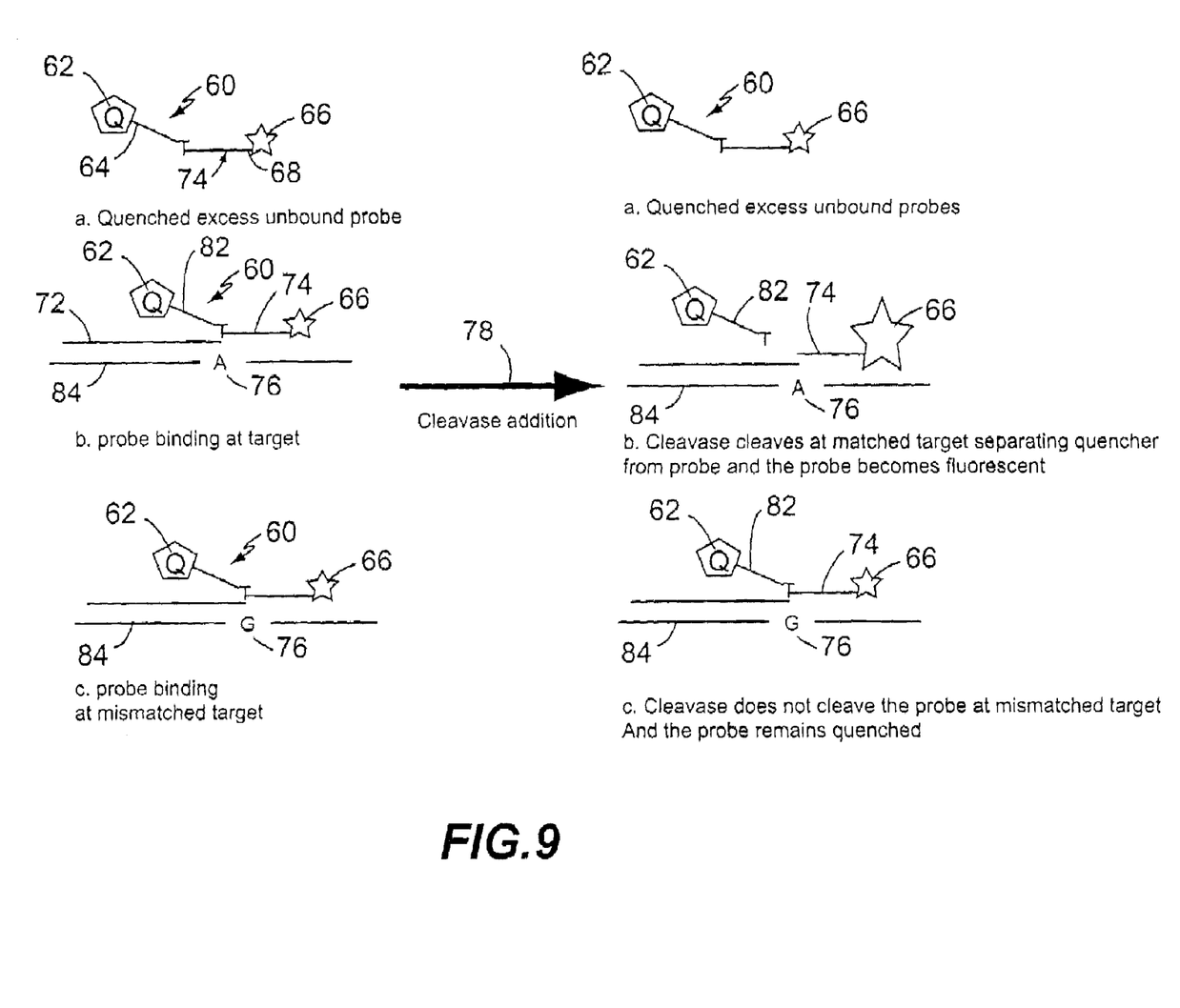
FIG. 9 pictorially depicts the application of a quencher capture reagent to genotyping using a modified cleavase assay.

The quenching method of the invention can be applied to a two-probe modified cleavase assay. FIG. 9 schematically depicts a two-probe modified Cleavase assay for genotyping. A signaling probe 60 contains a quencher 62 at the 5' end 64 and a fluorophore 66 at 3' end 68 (depending on the total length of oligonucleotide, the label may be moved to a internal position to improve quenching efficiency). Upon the binding of left invader oligonucleotide 72 and signaling probe 74 to a specific mutation, in this case a single nucleotide polymorphism (SNP) 76 on genomic DNA, enzyme 78, such as Cleavase VIII, cleaves flap 82 at 5' 64 of T opposite SNP target A 76 and separates quencher 62 from fluorophore 66 to enable fluorescence to be detected. If a single-base mismatch at SNP position 76 is formed between the 3' terminal base 64 of invader oligonucleotide 72 and genomic target 84, the cleavage of flap 82 will not occur. As a result, no fluorescence will be detected.

A two-probe approach may be designed to reduce non-specific target binding and fluorescence background of unbound probes. A two-probe approach refers to the case where two hybridization probes are used to label one mutation. The requirement of both invader oligonucleotide 72 (left of SNP) and signaling oligonucleotide 74 (right oligonucleotide) at a correct SNP target 76 to generate a fluorescence signal (after cleavage) increases labeling specificity. The non-fluorescent invader oligonucleotide 72 is added in high concentration (~100 nM) to ensure complete hybridization to target 84, and the signaling oligonucleotide 74 is added at ~500 pM. Furthermore, the signaling oligonucleotide 74 bears a 5' quencher molecule 62 and 3' fluorescent label 66, a design to quench fluorescence of unbound or un-cleaved probes. Bound probes are rendered fluorescent by the removal of quencher 62 by the action of enzyme 78 only when invader oligonucleotide 72 and signaling oligonucleotide 74 are pairing with the correct SNP targets 76 on genomic DNA 84.

Figure 10:
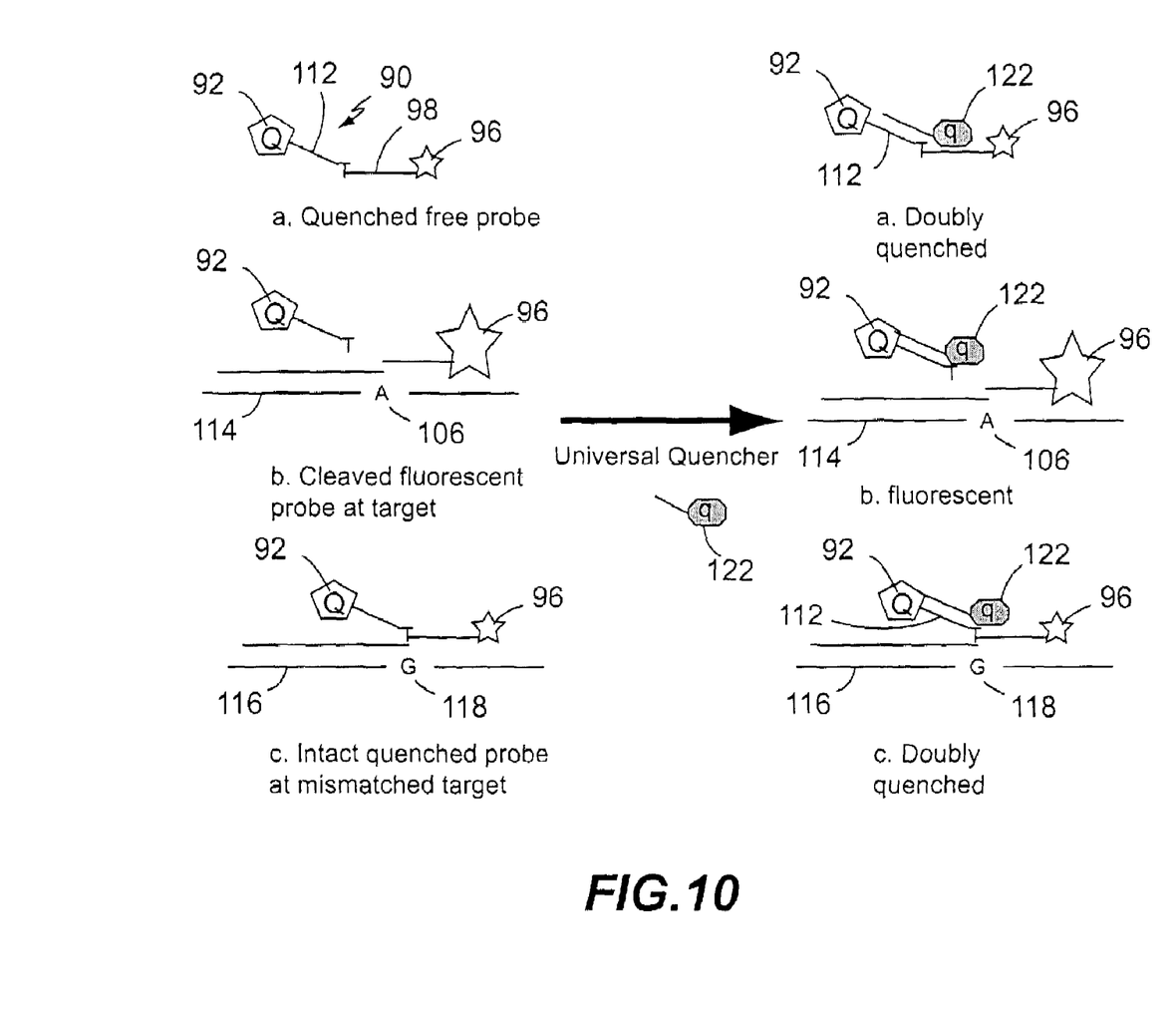
FIG. 10 pictorially depicts the use of a secondary quencher capture reagent to further reduce background fluorescence.

A secondary quencher oligonucleotide complementary to signaling oligonucleotide (right oligonucleotide) may be used to further quench the fluorescence from unbound probes. FIG. 10 schematically depicts a secondary quencher oligonucleotide scheme to further reduce background fluorescence from unbound probes and probes bound to mismatched targets. A universal secondary quencher oligonucleotide 122 can be used to capture the universal flap sequence 112 of signaling oligonucleotides. A secondary quencher oligonucleotide 122 that is complementary to flap 112 of signaling probes 90 will be added to further quench the fluorescence due to the residual fluorescence of unbound signaling probes 90, as illustrated in FIG. 10. For instance, if the first quencher 92 on 5' flap region 112 can quench the 3' fluorophore by a factor of 10, addition of another complementary quenching oligonucleotide 122 to signaling sequence 90 may give another 10-fold fluorescence background reduction (a total of 100-fold reduction of background and the use of 500 pM probe gives only 5 pM equivalent). Therefore, the use of both quenchers 92, 112 could reduce the fluorescence background more efficiently than single quencher.

To reduce the cost and complexity of large-scale genomic analysis, the development of a universal quencher capture oligonucleotide that hybridizes a universal 5' flap of the signaling oligonucleotide is preferred. In order to do that, the 5' flap of signaling oligonucleotides can be designed to be a non-human universal tag sequence (e.g, a universal nonhuman 15 mer), and a complementary DNA quenching oligonucleotide. A universal quenching oligonucleotide can be used to capture the tag of the signaling oligonucleotide (FIG. 10).

The efficiency of quenching depends on the configuration and physical distance of quencher and fluorophore. The best quenching result is typically achieved if the signaling oligonucleotide and quenchers are close together. However, this requires the quenching molecule of the capture oligonucleotide (complementary to the 5' flap) and the quenching molecule on the signaling oligonucleotide to be close to the fluorescent dye. The fluorescent labels on the different positions on the signaling oligonucleotide are paired with quencher molecules on the different positions to optimize for the best signaling oligonucleotide/quenching configurations.

In another embodiment of NA detection applications, NA analogs can be substituted for DNA or RNA probes. Hundreds of NA analogs and chimeras have been developed which have superior binding affinities for native nucleic acid targets, increased nuclease resistance, improved cellular uptake properties and/or other desirable features compared to naturally occuring NA probes (De Mesmaeker, A. et al., *Antisense Oligonucleotides.* Accounts of Chemical Research, 1995, 28(9), pp. 366–374; Leumann, C. J., *DNA Analogues: From Supramolecular Principles to Biological Properties.* Bioorganic & Medicinal Chemistry, 2002, 10(4), pp. 841–854.) For example, minor groove binder—conjugated DNA (Afonina, I. A. et al., *Minor Groove Binder-Conjugated DNA Probes for Quantitative DNA Detection by Hybridization-Triggered Fluorescence.* BioTechniques, 2002, 32(4), pp. 940–949), 2'-O-methyl oligoribonucleotide (Majlessi, M. et al., *Advantages of 2'-O-Methyl Oligoribonucleotide Probes for Detecting RNA Targets.* Nucleic Acids Research, 1998, 26(9), pp.2224–2229), PNA (Peptide Nucleic Acid) (Dueholm, K. L. et al.; *Properties and Applications of PNA (Peptide Nucleic-Acid).* New Journal of Chemistry, 1997, 21(1), pp. 19–31; Eriksson, M. and P. E. Nielsen, *PNA Nucleic-Acid Complexes: Structure; Stability and Dynamics.* Quarterly Reviews of Biophysics, 1996, 29(4), pp. 369–394; Gambari, R., *Applications of peptide nucleic acids (PNA) in molecular medicine and biotechnology:* Preface. Minerva Biotecnologica, 1999, 11(3), pp. 161–162), and LNA (Locked Nucleic Acid) probes (Singh, S. K., et al., *LNA (locked nucleic acids): synthesis and high-affinity nucleic acid recognition*, Chemical Communications, 1998(4), pp. 455–456; Wengel, J., LNA (*Locked Nucleic Acid,.* Abstracts of Papers of the American Chemical Society, 1999, 217(pt.1), pp. 3-CARB; all incorporated herein by reference, may be used. These are stronger DNA binders that hybridize efficiently at lower probe concentrations. In the case of PNA, PNA is capable of hybridizing to a target in the presence of denaturing reagents such as 7 M Urea. The success of PNA probes for genomic DNA target hybridization has been demonstrated on corn genomic DNA (250 fM target and 100 pM PNA probes) samples (Castro, A. et al., supra). PNA or LNA is not preferred because of probe sequence design restrictions (e.g., can not have 4 Gs in a row, can not have more than 40% GC content), dramatically increased cost, and other limitations, such as probe/target adducts that are not good substrates for enzyme modification.

In the above examples the present invention provides the following advantages:
1) The fluorescent hybridization probes can be added in large excess to the target sequence fragment concentration to increase the speed of the hybridization reaction. This improves the sensitivity of the assay at low target sequence concentrations and reduces the amount of time required to prepare samples for analysis.
2) Addition of non-fluorescent quencher oligonucleotides reduces excess, unbound probe fluorescence without the need for a physical separation of unbound fluorescent hybridization probe from the probe-target adducts prior to analysis.

Potential commercial applications include any that use fluorescence detection and for which a specific quenching strategy aimed at reducing unbound probe emission can be adopted. Some examples include: (1) direct determination of haplotypes in unamplified genomic DNA samples using single-molecule fluorescence spectroscopy; (2) luminescence detection of nucleic acid sequences (DNA or RNA) in clinical samples for disease diagnostics and the determination of optimal treatment strategies; (3) luminescence detection and/or quantification of any other ligand/receptor interaction in a target/probe binding assay.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for reducing background luminescence from a solution containing unbound luminescent probes, each having a first molecule that attaches to a target molecule and having an attached luminescent moiety, and luminescent probe/target adducts, comprising:
   (a) forming quenching capture reagent molecules capable of forming an adduct with the unbound luminescent probes and having an attached quencher material effective to quench luminescence of the luminescent moiety; and
   (b) placing the quencher material of the capture reagent molecules in a solution of the luminescent probe/target adducts and in a proximity to the luminescent moiety of the unbound luminescent probes, after the formation of the luminescent probe/target adducts, to quench luminescence from the luminescent moiety when the luminescent moiety is exposed to exciting illumination.

2. The method of claim 1, wherein the luminescent moiety is a fluorescent moiety.

3. The method of claim 1, wherein the luminescent probes are introduced in a concentration greater than a concentration of the target molecules to form the solution of luminescent probe/target adducts with an excess of luminescent probes, and
   quenching capture reagent is introduced in excess of the amount of luminescent probe/target adducts.

4. The method of claims 1, 2 or 3, wherein the target is selected from the group consisting of double—and single stranded nucleic acid oligomers, peptides, proteins, lipids, and carbohydrates.

5. The method of claims 1, 2 or 3, wherein the luminescent probes are selected from the group consisting of luminescence emitting moiety-labeled nucleic acid and nucleic acid analog oligomers, peptides, proteins, lipids, and carbohydrates.

6. The method of claims 1, 2 or 3, wherein the quenching capture reagent molecule is selected from the group consisting of quencher moiety-labeled nucleic acid and nucleic acid analog oligomers, peptides, proteins, lipids, and carbohydrates.

7. The method of claims 1, 2 or 3, wherein the luminescent moiety of the probe is fluorescent and is selected from the group consisting of organic dyes, proteins, nanostructures, and metals.

8. The method of claims 1, 2 or 3, wherein the quenching moiety of the capture reagent molecule is selected from the group consisting of organic dyes, proteins, nanostructures, and metals.

9. The method of claim 1, wherein
the probe is formed as a first oligonucleotide sequence labeled with the luminescent moiety;
the quenching capture reagent molecules are formed as a nucleotide sequence complementary to the first oligonucleotide sequence and labeled with the quencher moiety; and,
hybridization conditions are established to hybridize quenching capture reagent molecules to the unbound ones of the luminescent oligonucleotide probes to place the quencher moiety proximate the luminescent moiety.

10. The method of claim 9, wherein
the first oligonucleotide sequence is labeled at the 5' end with the luminescent moiety; and,
the nucleotide sequence complementary to the first oligonucleotide sequence is labeled at the 3' end with the quencher moiety.

11. The method of claim 10, wherein the luminescent probe/target adducts are formed by providing a first concentration of the target molecules; adding a second concentration of the probes to the target, where the second concentration is at least 100 times greater than the first concentration;
and establishing, hybridization conditions that specifically hybridize the probes to the target.

12. The method of claim 1, wherein the step of placing the quencher moiety of the capture reagent molecules in a proximity to the luminescent moiety of the luminescent probes includes the steps of:
forming a signal probe having a first oligonucleotide sequence that is complementary to a nucleotide sequence of the target and having a luminescent label at the 3' end and a nucleotide at the 5' end that is complementary to a single nucleotide polymorphism (SNP) at one end of the target nucleotide sequence;
forming the quenching capture reagent molecule effective to attach to the 5' end of the signal probe and having a nucleotide sequence that does not hybridize adjacent to the SNP and that has the quencher moiety attached to the 5' end of the quenching capture reagent molecule so that the quencher moiety and the luminescent label are in sufficient proximity to quench luminescence from the luminescent moiety.

13. The method of claim 12, further including the steps of:
forming an invader oligonucleotide probe effective to hybridize to the SNP and to the target nucleotide sequence adjacent the SNP and the first oligonucleotide sequence;
establishing hybridization conditions effective to specifically hybridize the invader oligonucleotide probe and first oligonucleotide sequence to the target nucleotide sequence; and
introducing an enzyme effective to cleave the signal probe at the SNP location to separate the first oligonucleotide sequence and quenching capture reagent molecule when there is a nucleotide match at the SNP location from the first oligonucleotide sequence, invader sequence, and target sequence, and hybridization occurs so that the quenching capture reagent molecule is removed from proximate the luminescent moiety and the luminescent moiety luminesces when excited by an exciting illumination and whereby the signal probe remains intact if there is a nucleotide mismatch at the SNP location and luminescence of the luminescent moiety of the unbound signal probe remains quenched.

14. A method for identifying SNPs comprising:
(a) identifying a target DNA nucleotide sequence having a SNP site;
(b) forming an oligonucleotide probe complementary to the target sequence, having a luminescent label at the 3' end and a nucleotide at the 5' end that is complementary to the SNP site;
(c) establishing hybridization conditions to specifically hybridize the oligonucleotide probe to the target sequence when a SNP match is present, wherein the probe does not hybridize to the target sequence if a SNP match is not present;
(d) following hybridization of oligonucleotide probe to the target sequence, introducing quenching capture reagent molecules having a nucleotide sequence complementary to the oligonucleotide probe and having a quencher moiety attached to the 5' end effective to quench luminescence when placed in an effective proximity to the luminescent label;
(e) establishing hybridization conditions to specifically hybridize quenching capture reagent molecules to oligonucleotide probes that did not hybridize to the target sequence;
(f) exciting the luminescent moiety whereby the probes hybridized to the target sequences luminesce and the probes hybridized to the quenching capture reagent molecules do not luminesce; and
(g) detecting the presence or absence of luminescence to determine the presence or absence of a SNP match.

15. The method of claim 1, 2, 3, 9, 10, 11, 12 or 13, wherein the first molecule of the fluorescent probes is selected from the group consisting of 2'-O-methyl RNA, peptide nucleic acid, locked nucleic acid, iso-cytosine, iso-guanine, modified nucleic acid, and nucleic acid-protein chimeras.

16. method of claim 1, 2, 3, 9, 10, 11, 12 or 13, wherein the quenching capture reagent molecules include molecules selected from the group consisting of 2'-O-methyl RNA, peptide nucleic acid, locked nucleic acid, iso-cytosine, iso-guanine, modified nucleic acid, and nucleic acid-protein chimeras.

* * * * *